United States Patent
Takakura

(10) Patent No.: US 8,697,038 B2
(45) Date of Patent: Apr. 15, 2014

(54) OIL-IN-WATER TYPE EMULSION SUNSCREEN COSMETIC COMPOSITION

(75) Inventor: Tomiko Takakura, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 97 days.

(21) Appl. No.: 13/521,559

(22) PCT Filed: Dec. 27, 2010

(86) PCT No.: PCT/JP2010/073560
§ 371 (c)(1),
(2), (4) Date: Sep. 5, 2012

(87) PCT Pub. No.: WO2011/092992
PCT Pub. Date: Aug. 4, 2011

(65) Prior Publication Data
US 2013/0011348 A1    Jan. 10, 2013

(30) Foreign Application Priority Data
Jan. 29, 2010   (JP) .................................. 2010-017893

(51) Int. Cl.
*A61K 8/00*    (2006.01)
(52) U.S. Cl.
USPC .............................................. 424/59; 424/60
(58) Field of Classification Search
None
See application file for complete search history.

(56) References Cited

U.S. PATENT DOCUMENTS

| | | | |
|---|---|---|---|
| 2007/0031348 A1* | 2/2007 | Staeb et al. | 424/47 |
| 2009/0163616 A1* | 6/2009 | Ishikubo et al. | 523/105 |
| 2009/0208541 A1* | 8/2009 | Gesztesi et al. | 424/401 |

FOREIGN PATENT DOCUMENTS

| | | |
|---|---|---|
| EP | 1283031 | 2/2003 |
| JP | 9-235216 | 9/1997 |
| JP | 2004-083541 | 3/2004 |
| JP | 2011-157282 | 8/2011 |
| JP | 4863411 | 11/2011 |

OTHER PUBLICATIONS

PCT/JP2010/073560 International Search Report mailed Apr. 5, 2011, 1 page—Japanese, 1 page—English.
JP 2010-017893, Decision to Grant a Patent mailed Nov. 4, 2011, 3 pages—English, 3 pages—Japan.
JP 2010-017893, Written Argument submitted Apr. 19, 2011, 1 page—English, 1 page—Japan.
JP 2010-017893, Written Amendment submitted Apr. 19, 2011, 2 pages—English, 2 pages—Japan.
JP 2010-017893Notice of Reasons for Rejection mailed Mar. 31, 2011, 2 pages—English, 2 pages—Japan.
Certificate of Translations dated Aug. 13, 2012, 5 pages—English.
Japanese Pat. No. 4863411—Granted Claims, 1 page—English, Jan. 25, 2012.

* cited by examiner

*Primary Examiner* — David J Blanchard
*Assistant Examiner* — Tigabu Kassa
(74) *Attorney, Agent, or Firm* — Andrew F. Young, Esq.; Lackenbach Siegel, LLP

(57) ABSTRACT

An oil-in-water type emulsion sunscreen cosmetic composition having improved ultraviolet blocking capability, excellent emulsion stability and good usability. The oil-in-water type emulsion sunscreen cosmetic composition is characterized by containing (A) 1-7.5% by mass of octyl methoxycinnamate, (B) 0.5-4% by mass of t-butyl methoxybenzoyl methane and/or 2-hydroxy-4-methoxybenzophenone, (C) 0.5-3% by mass of a polyoxyethylene-polyoxyalkylene alkyl ether block polymer having a specific structure and (D) not less than 10% by mass of a nonpolar oil relative to the total amount of the oil component. The oil-in-water emulsion sunscreen cosmetic composition is also characterized by having an average emulsion particle diameter of not more than 700 nm.

1 Claim, No Drawings

OIL-IN-WATER TYPE EMULSION SUNSCREEN COSMETIC COMPOSITION

CROSS REFERENCE TO RELATED APPLICATIONS

This application claims priority to International Ser. No. PCT/JP2010/073560 filed Dec. 27, 2010, the entire contents of which are incorporated herein fully by reference, which in turn claims priority to JP Ser. No. JP 2010-017893, filed on Jan. 29, 2010.

TECHNICAL FIELD

The present invention relates to an oil-in-water type emulsion composition. More specifically, it relates to an oil-in-water type emulsion sunscreen cosmetic composition which exhibits excellent ultraviolet protection ability by stably containing a large amount of an ultraviolet absorbent, i.e., by selecting and adding a combination of specific ultraviolet absorbent, a surface active agent with specific structure, and nonpolar oil, while having good usability.

BACKGROUND ART

A sunscreen cosmetic composition cuts off ultraviolet rays emitted from the sun, and therefore is used for protecting the skin from harmful damages caused by ultraviolet rays. A base type of the cosmetic composition includes an emulsion type, a lotion type, and an oil type. Of these, an oil-in-water type emulsion is widely used as it gives a moist feeling on use and can be formulated into a broad range of products including a low SPF product and a high SPF product (Non-Patent Document 1).

Meanwhile, the ultraviolet absorbent added to a sunscreen cosmetic composition is classified into an oil soluble type and a water soluble type. In this regard, to obtain high protection based on absorption of ultraviolet rays in the UVA region (wavelength of 320 to 400 nm) and UVB region (wavelength of 290 to 320 nm), it is necessary to add a UVB absorbent and a UVA absorbent with a good balance between them.

However, to improve the protection ability against ultraviolet rays by adding a large amount of an oil soluble ultraviolet absorbent, a surface active agent also needs to be used in a large amount to ensure emulsion stability. As a result, there is a tendency that a problem in use, such as oily feeling or stickiness is caused. In particular, the UVA absorbent has a problem of having lowered emulsion stability when its concentration is high in oil.

For example, it is described in Patent Document 1 that, by using polysaccharide derivatives having a specific substituent group, polyols, and a non-ionic surface active agent with HLB of 4 to 9 in combination with an oil component to stably add a material with poor solubility in an oil-in-water type emulsion composition, the emulsion particles can be more finely and homogeneously dispersed compared to conventional techniques. However, the ultraviolet absorbent is not discussed as a material with poor solubility.

In Patent Document 2, an oil-in-water type emulsion cosmetic composition which contains stably dispersed various oil components and has good feel, emollient effect and moisturizing effect on the skin by using polyoxyethylene addition type castor oil and polyoxyethylene addition type sorbitan fatty acid ester as an emulsifying agent is described. However, the ultraviolet absorbent is not discussed as an oil component to be added.

In Patent Document 3, a sunscreen composition as an emulsion containing 4,4-diaryl butadiene based ultraviolet screening agent which is prepared by adding ionic polymer particles instead of using a surface active agent, in which an oil droplet has a diameter of 500 nm or less, is described.

PRIOR ART DOCUMENTS

Patent Document

Patent Document 1: JP-A 2006-182724
Patent Document 2: JP-A 10-95707
Patent Document 3: JP-A 2004-315532

Non-Patent Literature

Non-Patent Document 1: "New Cosmetic Science, 2nd edition", Mitsui Takeo, Nanzando, 2001, pp 497-504

SUMMARY OF INVENTION

Problems to be Solved by the Invention

The invention is devised under the circumstances described above, and object of the invention is to provide an oil-in-water type emulsion sunscreen cosmetic composition which has improved ultraviolet protection ability by containing a large amount of an ultraviolet absorbent, while having excellent emulsion stability and good usability.

Means for Solving the Problem

To solve the problems described above, inventors of the invention conducted intensive studies. As a result, it was found that, by selecting t-butyl methoxy dibenzoyl methane and/or 2-hydroxy-4-methoxy benzophenone as an ultraviolet absorbent in addition to octyl methoxy cinnamate and by using in combination a surface active agent with specific structure and nonpolar oil to have average emulsion particle diameter of 700 nm or less, ultraviolet protection ability can be improved while maintaining the stability. The invention is completed accordingly.

That is, the present invention is to provide:
an oil-in-water type emulsion sunscreen cosmetic composition, containing
(A) 1 to 7.5% by mass of octyl methoxycinnamate,
(B) 0.5 to 4% by mass of t-butyl methoxy dibenzoyl methane and/or 2-hydroxy-4-methoxybenzophenone,
(C) 0.5 to 3% by mass of a polyoxyethylene/polyoxyalkylene alkyl ether block copolymer which is represented by the following formula (1) or (2):

$$R_1O\text{-}(AO)m\text{-}(EO)n\text{-}H \quad (1)$$

[in the formula (1), $R_1$ is a hydrocarbon group having 16 to 18 carbon atoms, AO is an oxyalkylene group having 3 to 4 carbon atoms, AO and EO are bonded in block form, m and n each represent an average addition mole number of AO and EO, respectively, and m>4, n>10, and n>m];

$$R_2O\text{-}(AO)p\text{-}(EO)q\text{-}R_3 \quad (2)$$

[in the formula (2), $R_2$ and $R_3$, which may be the same or different from each other, each represent a hydrocarbon group having 1 to 4 carbon atoms, AO is an oxyalkylene group having 3 to 4 carbon atoms, EO is an oxyethylene group, AO and EO are bonded in block form, p and q each represent an average addition mole number of AO and EO, respectively, and 1≤p≤70, 1≤q≤70, and 0.2<(q/(p+q))<0.8], and (D) 10% by mass or more of nonpolar oil per the total amount of the oil component, wherein an average emulsion particle diameter is 700 nm or less.

Effects of the Invention

Since a large amount of an ultraviolet absorbent, which has been believed to have poor emulsion stability, can be stably added to the oil-in-water type emulsion sunscreen cosmetic composition of the invention, the cosmetic composition of the invention exhibits excellent ultraviolet protection ability. Further, the cosmetic composition of the invention also has excellent usability in that it has moist feeling without stickiness.

MODES FOR CARRYING OUT THE INVENTION

The oil-in-water type emulsion composition of the invention contains octyl methoxycinnamate (ethyl hexyl methoxy cinnamate) (i.e., component A). Octyl methoxycinnamate is an ultraviolet (UVB) absorbent which is present as oil at room temperature. According to the invention, commercially available products such as "PARSOL MCX" (trade name, manufactured by DSM Nutrition Japan K. K.) can be used, for example.

Addition amount of octyl methoxycinnamate in the composition of the invention is 1 to 7.5% by mass, preferably 2 to 7% by mass, and more preferably 4 to 6% by mass. When the addition amount is less than 1% by mass, ultraviolet absorption is not obtained at a sufficient level. On the other hand, when it is used in an amount of more than 7.5% by mass, the feeling on use (i.e., stickiness) and stability tend to get deteriorated.

The oil-in-water type emulsion cosmetic composition of the invention is characterized by containing t-butyl methoxy dibenzoyl methane and/or 2-hydroxy-4-methoxy benzophenone (i.e., component B) in addition to octyl methoxycinnamate (component A).

Both of t-butyl methoxy dibenzoyl methane and 2-hydroxy-4-methoxy benzophenone are an ultraviolet (UVA) absorbent, and each of them is commercially available as "PARSOL 1789" (trade name, manufactured by DSM Nutrition Japan K. K.) and "Uvinul M40" (trade name, manufactured by BASF K. K.), respectively. Those commercially available products can be also used for the invention.

The total addition amount of t-butyl methoxy dibenzoyl methane and/or 2-hydroxy-4-methoxy benzophenone in the cosmetic composition of the invention is 0.5 to 4% by mass, preferably 1 to 4% by mass, and more preferably 1.5 to 3% by mass, in both cases of being used singly or used in mixture of them. When the addition amount is less than 0.5% by mass, ultraviolet absorption is not obtained at a sufficient level. On the other hand, when it is used in an amount of more than 4% by mass, the stability tends to get deteriorated.

The cosmetic composition of the invention is characterized in that it uses at least one of the polyoxyethylene/polyoxyalkylene alkyl ether block copolymer (herein below, referred to as "block copolymer") represented by the following formula (1) or (2) as an emulsifying agent.

$$R_1O\text{-}(AO)m\text{-}(EO)n\text{-}H \quad (1)$$

In the formula (1), $R_1$ is a hydrocarbon group having 16 to 18 carbon atoms, and preferably a saturated or unsaturated aliphatic hydrocarbon group. Examples thereof include palmityl, stearyl, isostearyl, oleyl, and linoleyl.

AO is an oxyalkylene group having 3 to 4 carbon atoms, and examples thereof include an oxypropyl group and an oxybutyl group. EO is an oxyethylene group.

In the formula (1), AO and EO should be bonded in block form. If they are bonded in random form, formulation stability is not obtained at a sufficient level. The addition order of alkylene oxide and ethylene oxide is not specifically designated. Further, the block form includes not only a two-stage block but also a three-stage block or higher.

m and n represent an average addition mole number of PO and EO, respectively, and m>4, n>10, and n>m.

Molecular weight of the block copolymer of the formula (1) is preferably 800 or more, and more preferably 1500 or more. When the molecular weight is less than 800, the effect is low. Further, although the upper limit of the molecular weight is not specifically limited, there is a possibility that sticky feeling is yielded according to an increase in the molecular weight.

As the block copolymer represented by the formula (1), a commercially available product such as NIKKOL PSC44 (trade name, manufactured by Nikko Chemicals Co., Ltd.) can be used.

$$R_2O\text{-}(AO)p\text{-}(EO)q\text{-}R_3 \quad (2)$$

In the formula (2), $R_2$ and $R_3$, which may be the same or different from each other, each represents a hydrocarbon group having 1 to 4 carbon atoms, and preferably a saturated aliphatic hydrocarbon group. Examples thereof include methyl, ethyl, propyl, isopropyl, butyl, isobutyl, sec-butyl, and tert-butyl. More preferably, it is methyl or ethyl.

AO is an oxyalkylene group having 3 to 4 carbon atoms, and examples thereof include an oxypropyl group and an oxybutyl group. ED is an oxyethylene group.

In the formula (2), AO and EO are bonded in block form. If they are bonded in random form, formulation stability is not obtained at a sufficient level. The addition order of ethylene oxide and alkylene oxide is not specifically designated. Further, the block form includes not only a two-stage block but also a three-stage block or higher.

p and q represent an average addition mole number of AO and EO, respectively, and 1≤p≤70, 1≤q≤70, and 0.2<(q/(p+q))<0.8.

Molecular weight of the block copolymer of the formula (2) is preferably 1000 or more, and more preferably 3000 or more. When the molecular weight is less than 1000, the effect is low. Further, although the upper limit of the molecular weight is not specifically limited, there is a possibility that sticky feeling is yielded in accordance with an increase in the molecular weight.

The block copolymer of the formula (2) can be produced according to a method known in the field. For example, it can be obtained by performing addition polymerization of a compound having a hydroxy group with ethylene oxide and alkylene oxide having 3 to 4 carbon atoms and then performing an ether reaction of alkyl halide in the presence of an alkali catalyst (see, for example, JP-A 2004-83541), Specific examples of the block copolymer of the formula (2) include POE (14) POP (7) dimethyl ether, POE (17) POP (4) dimethyl ether, POE (10) POP (10) dimethyl ether, POE (7) POP (12) dimethyl ether, POE (15) POP (5) dimethyl ether, POE (25) POP (25) dimethyl ether, POE (27) POP (14) dimethyl ether, POE (55) POP (28) dimethyl ether, POE (22) POP (40) dimethyl ether, POE (35) POP (40) dimethyl ether, POE (50) POP (40) dimethyl ether, POE (36) POP (41) dimethyl ether, POE (55) POP (30) dimethyl ether, POE (30) POP (34) dimethyl ether, POE (25) POP (30) dimethyl ether, POE

(14) POB (7) dimethyl ether, POE (10) POP (10) diethyl ether, POE (10) POP (10) dipropyl ether, and POE (10) POP (10) dibutyl ether.

Meanwhile, POE, POP, and POB are the abbreviations of polyoxyethylene, polyoxypropylene, and polyoxybutylene, respectively.

Addition amount of the block copolymer (i.e., component C) is 0.5 to 3% by mass, preferably 0.5 to 2% by mass, and more preferably 0.5 to 1% by mass in the composition. Since a small amount of the block copolymer is enough to emulsify finely and stably an oil phase containing the component (A) and component (B), a stable oil-in-water type emulsion composition can be obtained without having stickiness caused by a surface active agent. However, when it is used in an excessively small amount, a stable oil-in-water type emulsion composition may not be easily obtained. On the other hand, when it is used in an excess amount, there is a tendency that sticky feeling is easily caused.

The cosmetic composition of the invention also contains nonpolar oil (i.e., component D) in an amount of 10% by mass or more, and preferably 20% by mass or more per total weight of the oil components.

According to the invention, the nonpolar oil is preferably oil generally known as nonpolar or weakly polar oil, and it is not specifically limited. For example, it is selected from hydrocarbon oil such as hydrogenated polydecene, mineral oil, and squalene.

The oil-in-water type emulsion cosmetic composition of the invention is also characterized in that the oil phase has an average emulsion particle diameter of not more than 700 nm. When the particle diameter is exceeding 700 nm, there is a tendency that the formulation stability or feeling on use is deteriorated.

As a method for emulsification, any method can be used as long as the oil phase is finely emulsified extended to 700 nm or less. Examples of the method include a high pressure emulsification or micro emulsification which uses a hydrophilic solvent such as polyhydric alcohol in the presence (or absence) of a small amount of water (for example, Japanese Patent Application Publication No. 57-29213 and JP-A No. 2006-182724), but not limited thereto.

Examples of a specific production method that can be suitably used include a method including mixing part of water, an oil phase component, and an emulsifying agent, emulsifying them by using a high pressure emulsifying machine, and adding and mixing other components, and a method including mixing part of an aqueous phase and an emulsifying agent, adding to the mixture a solution in which an oil component is added and dissolved, emulsifying them by using a homomixer, and adding and mixing other components to the resulting emulsified product.

In addition to the essential components described above, the cosmetic composition of the invention may be added with other components that can be added to a cosmetic composition, unless the effect of the invention is not particularly impaired. Examples of other components that can be suitably added, if necessary, include a powder component, liquid oil components, solid oil components, bee wax, hydrocarbons, higher fatty acids, higher alcohols, esters, silicones, an anionic surface active agent, a cationic surface active agent, an amphoteric surface active agent, a non-ionic surface active agent, a moisturizing agent, a water soluble polymer, a tackifying agent, a filming agent, an ultraviolet absorbent, an ultraviolet scattering agent, a metal ion sequestering agent, lower alcohols, polyhydric alcohols, sugars, amino acids, organic amines, polymer emulsion, a pH adjusting agent, a skin nutrient, vitamins, an anti-oxidizing agent, an anti-oxidizing aid, fragrance, and water.

The cosmetic composition of the invention may contain an organic ultraviolet absorbent other than the component (A) and component (B) described above. Examples of the organic ultraviolet absorbent that can be added include an oil-based ultraviolet absorbent that is generally used for a cosmetic composition. Specific examples include a triazine-based ultraviolet absorbent (for example, bisresorcinyl triazine); octyl triazone (2,4,6-tris[4-(2-ethylhexyl oxycarbonyl) anilino]1,3,5-triazine); a benzoic acid-based ultraviolet absorbent (for example, para amino benzoic acid (herein below, referred to as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); an anthranilic acid-based ultraviolet absorbent (for example, homo mentyl-N-acetyl anthraniliate); a salicylic acid-based ultraviolet absorbent (for example, amyl salicylate, mentyl salicylate, homomentyl salicylate, octyl salicylate, phenyl salicylate, benzyl salicylate, and p-isopropanol phenyl salicylate); 3-(4'-methyl benzylidene)-d,l-camphor, 3-benzylidene-d,l-camphor; 2-phenyl-5-methyl benzoxazole; 2,2'-hydroxy-5-methylphenyl benzotriazole; 2-(2'-hydroxy-5'-t-octyl phenyl) benzotriazole; 2-(2'-hydroxy-5'-methylphenyl benzotriazole; dibenalazine; dianisoyl methane; 4-methoxy-4'-t-butyldibenzoylmethane; 5-(3,3-dimethyl-2-norbornylidene)-3-pentan-2-one, methylene bisbenzotriazole tetramethyl butyl phenol, and 4,4'-diaryl butadiene.

The oil-in-water type emulsion cosmetic composition of the invention can be applied for various cosmetic compositions which require an sunscreen activity, and therefore can be used not only for an emulsion, a creme, a cosmetic base formulation but also for a make-up cosmetic such as foundation and lipstick.

The cosmetic composition of the invention has moist feeling upon use that is intrinsic to an oil-in-water type emulsion composition and exhibits an excellent ultraviolet protection ability. As such, it is particularly suitable for the use as an oil-in-water type emulsion type sunscreen cosmetic composition.

EXAMPLES

Herein below, the invention is explained in greater detail in view of the specific examples. However, the invention is not limited to the Examples given below. Further, the addition amount mentioned in the following Examples indicates % by mass, unless specifically described otherwise.

Examples and Comparative Examples (Comp. Examples)

Emulsion composition having composition described in the following Table 1 was prepared and evaluated regarding the characteristics described below.
Items for Evaluation:
(1) Emulsion Stability
 The sample to be tested was stored for 1 month at 50° C. After that, the appearance was observed with a naked eye and evaluated based on the following criteria.
 ◯: there is no greasiness or creaming.
 x: there is greasiness or creaming.
(2) Average Emulsion Particle Diameter
 The particle size distribution of the emulsion particles was measured right after the preparation of a composition by using Zetasizer Nano ZS (trade name, manufactured by SYSMEX Corporation). In the Table, the descriptions "same or higher" and "same or lower" represent "700 nm or higher" and "700 nm or lower", respectively, as obtained according to naked eye observation.

(3) Feeling on Use (Stickiness)

Twenty women panelists applied each composition on their face by a hand. After that, they were asked with the questions regarding sticky feeling when the composition is absorbed in their skin and the evaluation was made based on the following criteria.

◯: Sixteen or more panelists found that there was no stickiness.

Δ: Six to fifteen panelists found that there was no stickiness.

x: Five or fewer panelists found that there was no stickiness.

(4) Ultraviolet Protection Ability

High: Absorbance at 310 nm is higher than the standard sample (in vivo measurement value for SPF30).

Std: Absorbance at 310 nm is higher than the standard sample (in vivo measurement value for SPF16).

Low: Absorbance at 310 nm is lower than the standard sample (in vivo measurement value for SPF16).

(5) Dissolution Stability

Oil components of each composition were dissolved and stored at low temperature (0° C.) for 1 month. After that, the precipitates were observed with a naked eye and evaluated based on the following criteria.

◯: no crystals precipitate.

x: crystals precipitate.

TABLE 1

|  | Example 1 | Example 2 | Example 3 | Example 4 | Comp. Example 1-1 | Comp. Example 1-2 |
|---|---|---|---|---|---|---|
| Water | Balance | Balance | Balance | Balance | Balance | Balance |
| Ethanol | 6 | 6 | 6 | 6 | 6 | 6 |
| Octyl methoxycinnamate | 5 | 5 | 5 | 5 | — | 5 |
| 2-Hydroxy-4-methoxy benzophenone | — | 2 | — | — | — | — |
| 4-Tert-butyl-4'-methoxy dibenzoyl methane | 2 | — | 2 | 2 | 2 | — |
| Dipropylene glycol | 3 | 3 | 3 | 3 | 3 | 3 |
| Ethyl hexyl triazone | 1 | 1 | 1 | 1 | 1 | 1 |
| Glycerin | 1 | 1 | 1 | 1 | 1 | 1 |
| Silica | 1 | 1 | 1 | 1 | 1 | 1 |
| PPG-8 ceteth-20 | 0.8 | — | 0.8 | 0.8 | 0.8 | 0.8 |
| PEG/PPG-50/40 dimethyl ether | — | 0.8 | — | — | — | — |
| Hydrogenated polydecene | 3 | 3 | — | 5 | — | — |
| Mineral oil | — | — | 3 | — | — | — |
| Diisopropyl sebacate | 2 | 2 | 2 | 2 | 2 | 2 |
| Isostearic acid | 0.2 | 0.2 | 0.2 | 0.2 | 0.2 | 0.2 |
| Carbomer K | 0.13 | 0.13 | 0.13 | 0.13 | 0.13 | 0.13 |
| Acrylic acid/Alkyl (C10-C30) acrylate copolymer | 0.07 | 0.07 | 0.07 | 0.07 | 0.07 | 0.07 |
| Trisodium edetate | 0.02 | 0.02 | 0.02 | 0.02 | 0.02 | 0.02 |
| BHT | 0.004 | 0.004 | 0.004 | 0.004 | 0.004 | 0.004 |
| Phenoxy ethanol | 0.3 | 0.3 | 0.3 | 0.3 | 0.3 | 0.3 |
| Methyl paraben | 0.15 | 0.15 | 0.15 | 0.15 | 0.15 | 0.15 |
| Emulsion stability | ◯ | ◯ | ◯ | ◯ | ◯ | ◯ |
| Emulsion particle diameter (nm) | 600 | 550 | 600 | 550 | X | Same or lower |
| Feeling on Use (stickiness) | ◯ | ◯ | ◯ | ◯ | ◯ | ◯ |
| UV protection ability | Std | Std | — | — | Low | Low |
| Dissolution stability | ◯ | ◯ | ◯ | ◯ | X | ◯ |

Ultraviolet protection ability of each composition was measured by using in vitro spectrophotometer U-4100 (trade name, manufactured by Hitachi Ltd.) and evaluated based on the following criteria.

The oil component (i.e., hydrogenated polybutene or mineral oil) of the composition of the Example 1 shown in the Table 1 was replaced with the oil described in the following Table 2, and the characteristics were evaluated in the same manner as above.

TABLE 2

|  | Comp. Example 2-1 | Comp. Example 2-2 | Comp. Example 2-3 | Comp. Example 2-4 | Comp. Example 2-5 | Comp. Example 2-6 |
|---|---|---|---|---|---|---|
| Triethyl hexanone | 3 | — | — | — | — | — |
| Isopropyl myristate | — | 3 | — | — | — | — |
| Cetyl ethyl hexanoate | — | — | 3 | — | — | — |
| Ethyl hexyl palmitate | — | — | — | 3 | — | — |
| Diphenyl siloxy phenyltrimethicone | — | — | — | — | 3 | — |
| Emulsion stability | X | X | X | X | X | X |
| Emulsion particle diameter (nm) | 1100 | 950 | 1040 | 1200 | 2000 | 3000 |
| Feeling on Use (stickiness) | ○ | ○ | ○ | ○ | ○ | ◎ |
| UV protection ability | — | — | — | — | — | — |
| Dissolution stability | ○ | ○ | ○ | ○ | ○ | ○ |

The surface active agent (i.e., PPG-8 ceteth-20 or PEG/PPG-50/40 dimethyl ether) of the composition of the Example 1 shown in the Table 1 was replaced with the surface active agent described in the following Table 3, and the characteristics were evaluated in the same manner as above.

TABLE 3

|  | Comp. Example 3-1 | Comp. Example 3-2 | Comp. Example 3-3 | Comp. Example 3-4 | Comp. Example 3-5 |
|---|---|---|---|---|---|
| PEG/PPG-35/40 dimethyl ether | 0.8 | — | — | — | — |
| Beheneth-30 | — | 0.8 | — | — | — |
| PEG-60 glyceryl isostearate | — | — | 0.8 | — | — |
| PEG-60 hydrogenated castor oil | — | — | — | 0.8 | — |
| PEG-100 hydrogenated castor oil | — | — | — | — | 0.8 |
| Emulsion stability | X | X | X | X | X |
| Emulsion particle diameter (nm) | 1000 | 1000 | 1680 | 1320 | 1000 |
| Feeling on Use (stickiness) | Δ | Δ | Δ | Δ | Δ |
| Ultraviolet protection ability | — | — | — | — | — |
| Dissolution stability | ○ | ○ | ○ | ○ | ○ |

|  | Comp. Example 3-6 | Comp. Example 3-7 | Comp. Example 3-8 | Comp. Example 3-9 |
|---|---|---|---|---|
| PEG-30 soy bean sterol | 0.8 | — | — | — |
| Dihydrocholeth-30 (wool) | — | 0.8 | — | — |
| Polysorbate 60 | — | — | 0.8 | — |
| Polysorbate 20 | — | — | — | 0.8 |
| Emulsion stability | X | X | X | X |
| Emulsion particle diameter (nm) | 1250 | 1250 | Same or higher | Same or higher |
| Feeling on Use (stickiness) | Δ | Δ | X | X |
| UV protection ability | — | — | — | — |
| Dissolution stability | ○ | ○ | ○ | ○ |

The addition amount of each essential component of the composition of the Example 1 shown in the Table 1 was changed to the amount described in the following Table 4, and the characteristics were evaluated in the same manner as above.

TABLE 4

|  | Comp. Example 4-1 | Comp. Example 4-2 | Comp. Example 4-3 | Comp. Example 4-4 | Comp. Example 4-5 |
|---|---|---|---|---|---|
| Octyl methoxy-cinnamate | 5 | 5 | 7.6 | 5 | 5 |
| 2-Hydroxy-4-methoxy benzophenone | 5.1 | — | — | — | 0.5 |
| 4-Tert-butyl-4'-methoxy dibenzoyl methane | — | 5.1 | 2 | 2 | — |
| PPG-8 ceteth-20 | 0.8 | 0.8 | 0.8 | 3.1 | 0.8 |
| Hydrogenated polydecene | 3 | 3 | 3 | 3 | 3 |
| Emulsion stability | X | X | X | ○ | ○ |
| Emulsion particle diameter (nm) | Same or higher | Same or lower | Same or higher | Same or lower | Same or lower |
| Feeling on Use (stickiness) | ○ | ○ | Δ | Δ | Δ |
| UV protection ability | High | High | High | — | Low |

TABLE 4-continued

| | Comp. Example 4-6 | Comp. Example 4-7 | Comp. Example 4-8 | Comp. Example 4-9 |
|---|---|---|---|---|
| Dissolution stability | X | X | X | X |

| | Comp. Example 4-6 | Comp. Example 4-7 | Comp. Example 4-8 | Comp. Example 4-9 |
|---|---|---|---|---|
| Octyl methoxy-cinnamate | 5 | 0.9 | 5 | 5 |
| 2-Hydroxy-4-methoxy benzo-phenone | — | — | — | — |
| 4-Tert-butyl-4'-methoxy dibenzoyl methane | 0.5 | 2 | 2 | 2 |
| PPG-8 ceteth-20 | 0.8 | 0.8 | 0.4 | 0.8 |
| Hydro-genated polydecene | 3 | 3 | 3 | 1 |
| Emulsion stability | ○ | ○ | X | X |
| Emulsion particle diameter (nm) | Same or lower | Same or higher | Same or higher | 1040 |
| Feeling on Use (stickiness) | Δ | Δ | ○ | ○ |
| Ultraviolet protection ability | Low | Low | — | — |
| Dissolution stability | ○ | X | ○ | ○ |

As it is clearly shown in the results given above, the oil-in-water type emulsion cosmetic composition of the invention may not provide sufficient ultraviolet protection ability and shows poor stability when any one of octyl methoxycinnamate or t-butyl methoxy dibenzoyl methane and/or 2-hydroxy-4-methoxy benzophenone is not included or it is contained in an amount less than the predetermined amount. On the other hand, when any one of them is included in an excess amount, there is a tendency that the stability is lowered while the ultraviolet protection ability is improved.

Further, there is also a tendency that the stability is lowered when nonpolar oil is not added in a sufficient amount.

Further, when a block copolymer with specific structure is not used or it is used in an amount less than the predetermined amount, the average emulsion particle diameter of 700 nm or less was not obtained and the stability also was degraded.

The invention claimed is:

1. An oil-in-water type emulsion sunscreen cosmetic composition, comprising:
    (A) 1 to 7.5% by mass of octyl methoxycinnamate;
    (B) 0.5 to 4% by mass of t-butyl methoxy dibenzoyl methane and/or 2-hydroxy-4-methoxybenzophenone;
    (C) 0.5 to 3% by mass of a polyoxyethylene/polyoxyalkylene alkyl ether block copolymer which is represented by the following formula (1) or (2):

$$R_1O\text{-}(AO)_m\text{-}(EO)_n\text{—}H \quad (1)$$

wherein in the formula (1), $R_1$ is a hydrocarbon group having 16 to 18 carbon atoms, AO is an oxyalkylene group having 3 to 4 carbon atoms, AO and EO are bonded in block forms, m and n each represents an average addition mole number of AO and EO, respectively, and m>4, n>10, and n>m;

$$R_2O\text{-}(AO)_p\text{-}(EO)_q\text{—}R_3 \quad (2)$$

wherein in the formula (2), $R_2$ and $R_3$, each represents a hydrocarbon group having 1 to 4 carbon atoms, AO is an oxyalkylene group having 3 to 4 carbon atoms, EO is an oxyethylene group, AO and EO are bonded in block forms, p and q each represents an average addition mole number of AO and EO, respectively, and 1≤p≤70, 1≤q≤70, and 0.2<(q/(p+q))<0.8; and
    (D) 10% by mass or more of nonpolar oil per the total amount of the oil component;
    wherein an average emulsion particle diameter is 700 nm or less.

* * * * *